US00PP30567P3

(12) United States Plant Patent
Ammerlaan

(10) Patent No.: US PP30,567 P3
(45) Date of Patent: Jun. 11, 2019

(54) ***CRASSULA* PLANT NAMED 'OVCRTR'**

(50) Latin Name: *Crassula ovata*
Varietal Denomination: OVCRTR

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 15/732,512

(22) Filed: Nov. 21, 2017

(65) Prior Publication Data

US 2018/0153081 P1 May 31, 2018

(30) Foreign Application Priority Data

Nov. 30, 2016 (QZ) ..... PBR 2016/2990

(51) Int. Cl.
*A01H 6/32* (2018.01)
*A01H 5/12* (2018.01)

(52) U.S. Cl.
USPC ..... Plt./373
CPC ..... *A01H 5/12* (2013.01)

(58) Field of Classification Search
USPC ..... Plt./373
CPC ..... A01H 6/32
See application file for complete search history.

*Primary Examiner* — Keith O. Robinson
(74) *Attorney, Agent, or Firm* — Samuel R. McCoy, Jr.

(57) ABSTRACT

A new and distinct variety of *Crassula* plant named 'OVCRTR' which is characterized by the combination of a broad spreading to upright growth habit, an abundance of dark green, narrowly spatulate foliage with an aspect which varies from convex to tubular, foliage apices which vary from obtuse to cup-shaped, and the stability of all characteristics from generation to generation.

3 Drawing Sheets

Latin name of the genus and species: The Latin name of the genus and species of the novel variety disclosed herein is *Crassula ovata.*

Variety denomination: The inventive variety of *Crassula* disclosed herein has been given the variety denomination 'OVCRTR'.

CROSS REFERENCE TO RELATED APPLICATIONS

This application claims priority to the Community Plant Variety Rights application number 2016/2990, filed Nov. 30, 2016, which is herein incorporated by reference.

BACKGROUND OF THE INVENTION

Parentage: 'OVCRTR' originated as a naturally occurring, whole-plant mutation of *Crassula* 'Hobbit' (not patented). In 2014, the inventor discovered the mutation at his commercial greenhouse in Bleiswijk, the Netherlands, growing amongst a cultivated population of 'Hobbit' plants. The mutation was noted for its compact habit and unique foliage characteristics and was subsequently isolated for further evaluation in order to confirm the distinctness and stability of the characteristics first observed. Upon confirmation of distinctness and stability, 'OVCRTR' was selected for commercialization.

Asexual Reproduction: Asexual reproduction of 'OVCRTR', by way of stem cuttings, was first initiated in 2014 at the inventor's commercial greenhouse in Bleiswijk, the Netherlands. Through five subsequent generations, the unique features of this cultivar have proven to be stable and true to type.

SUMMARY OF THE INVENTION

The cultivar 'OVCRTR' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'OVCRTR'. These characteristics in combination distinguish 'OVCRTR' as a new and distinct *Crassula* cultivar:

1. *Crassula* 'OVCRTR' exhibits a broad spreading to upright growth habit; and
2. *Crassula* 'OVCRTR' exhibits an abundance of thick dark green foliage; and
3. *Crassula* 'OVCRTR' exhibits narrowly spatulate foliage with an aspect which varies from convex to tubular; and
4. *Crassula* 'OVCRTR' exhibits foliage apices which vary from obtuse to cup-shaped.

BOTANICAL DESCRIPTION OF THE PLANT

Figure 1:
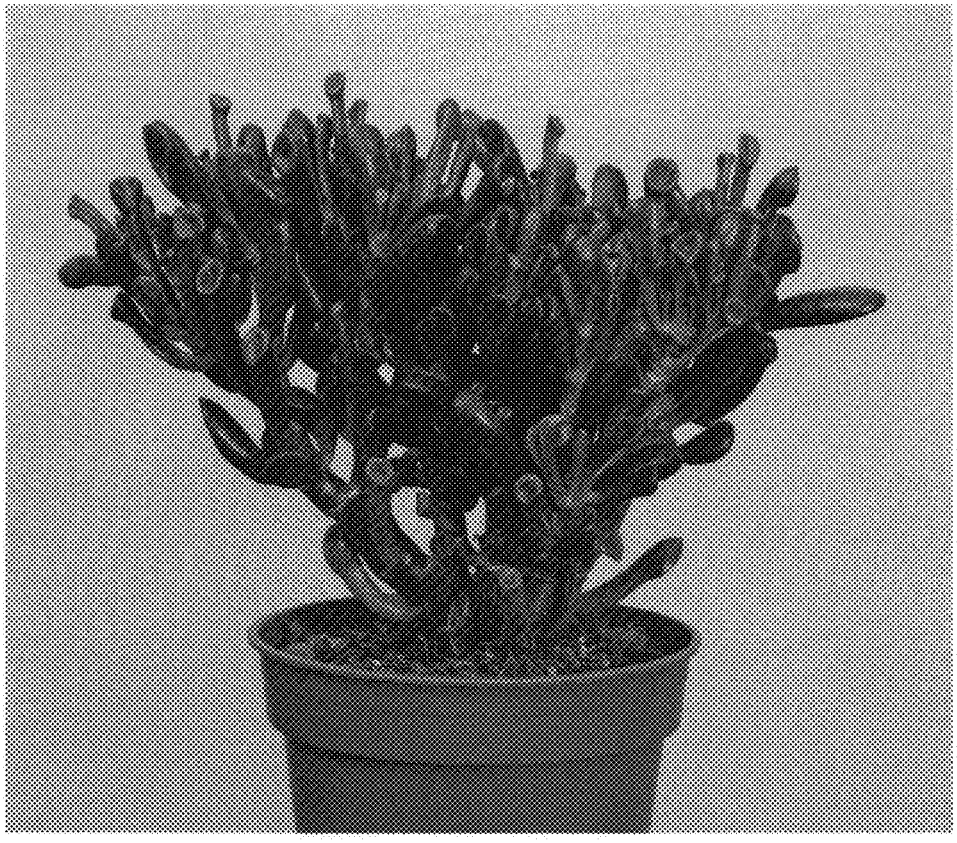
FIG. 1 illustrates, as nearly true as it is reasonably possible to make the same in color photographs of this type, an exemplary plant of 'OVCRTR' grown in a commercial greenhouse in Bleiswijk, The Netherlands. This plant is approximately 16 months old, shown planted in a 17 cm container.
Figure 2:
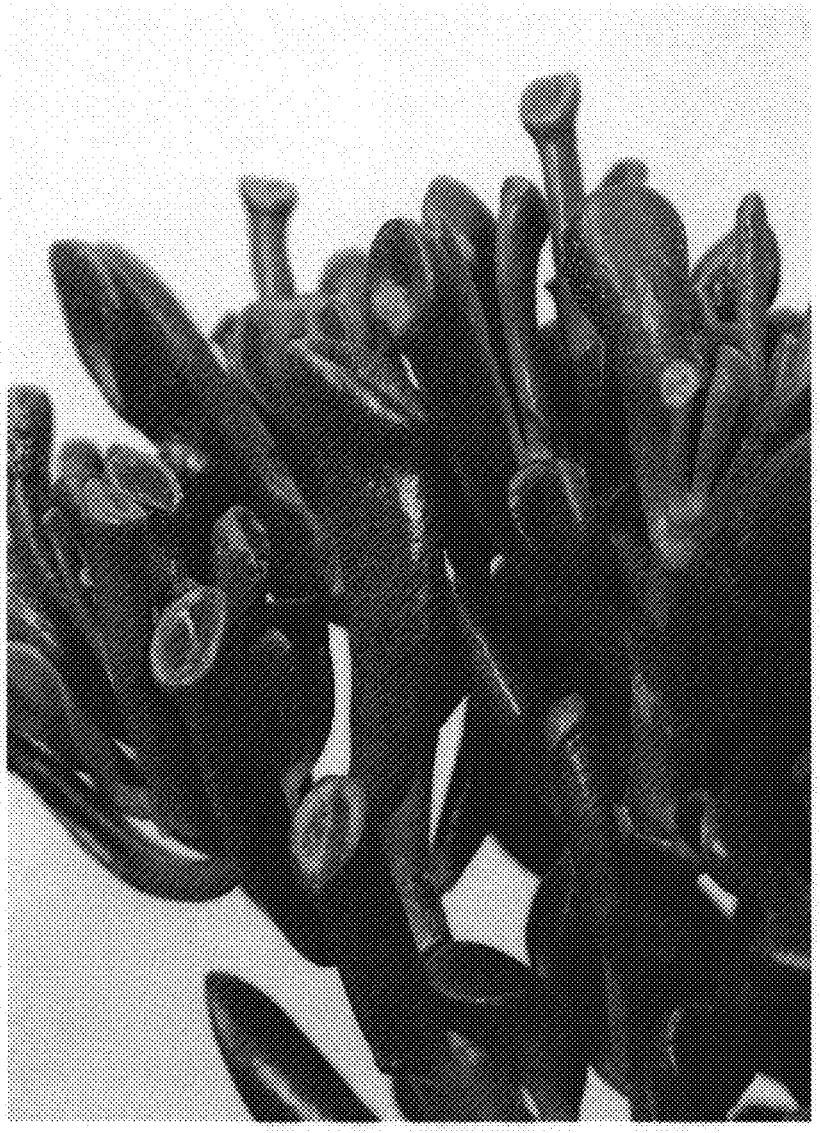
FIG. 2 illustrates, as nearly true as it is reasonably possible to make the same in color photographs of this type, the typical foliage of 'OVCRTR'.
Figure 3:
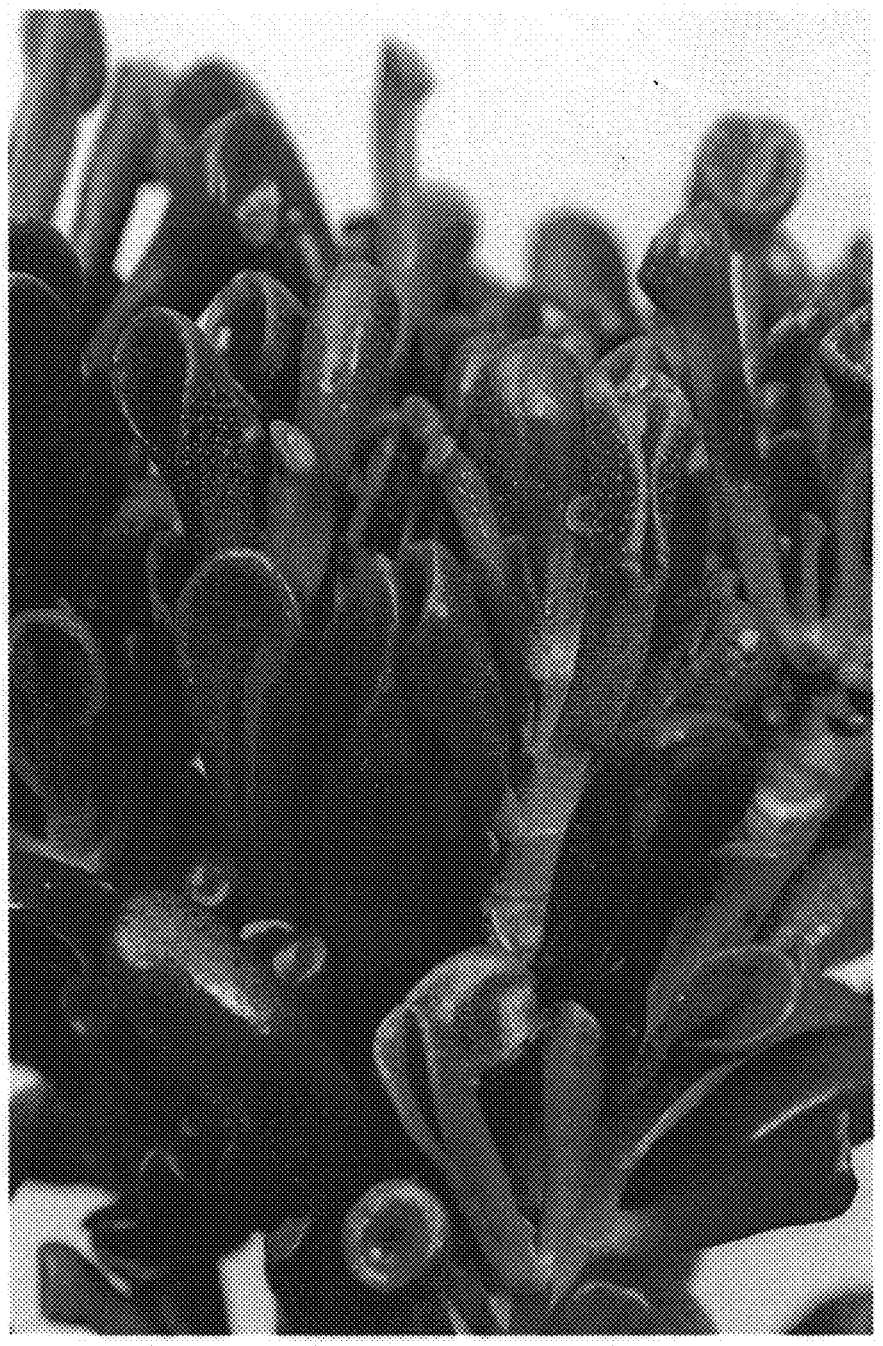
FIG. 3 illustrates, as nearly true as it is reasonably possible to make the same in color photographs of this type, the typical branches of 'OVCRTR'.

The following observations and measurements describe a 16 month-old 'OVCRTR' plant grown in 17 cm nursery pots at a commercial greenhouse in Bleiswijk, The Netherlands. Plants were produced using conventional greenhouse production protocols for *Crassula* which consisted of minimal overhead irrigation and no fertilizer applications. No pest or disease control measures were utilized in production. Plants were grown under shade (approximately 20,000 lux) and no photoperiodic treatments or artificial light was given to the plants.

Those skilled in the art will appreciate that certain characteristics will vary with older or, conversely, with younger plants. 'OVCRTR' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'OVCRTR' and comparisons with other varieties of *Crassula* are provided below.

Plant description:

*Growth habit*.—Broad spreading to upright perennial.

*Plant form*.—Irregular broad obovate to flattened globular.

*Average height*.—21.9 cm from the soil level to the top of the foliar plane.

*Plant spread*.—Average of 26.1 cm.

*Growth rate*.—Low to moderate.

*Plant vigor*.—Moderate.

*Propagation type*.—Stem cuttings.

*Time to produce a rooted cutting*.—Approximately 8 weeks to produce a rooted cutting at approximately 21 degrees Celsius.

*Time to produce a finished plant*.—21 months.

*Disease resistance*.—Neither resistance nor susceptibility to typical *Crassula* pests and diseases has been observed.

*Environmental tolerances*.—Adapt to, at least, USDA Zones 10 and 12 and temperatures as high as 40 degrees Celsius; low tolerance to rain; moderate to high tolerance to wind.

Root system:

*General*.—Dense and freely branched rooting; roots are moderately fibrous.

*Distribution in the soil profile*.—Shallow to moderately deep.

*Diameter of roots*.—0.1 cm on average.

*Texture*.—Smooth; no root hairs.

*Color*.—Greyed-yellow, nearest to RHS 166D.

Stem:

*General branching habit*.—Basally branching main stems; freely branching with lateral branches. Pinching isn't required but will improve branching.

*Main stems*.—Quantity of main stems per plant — 3. Length of main stems — Varying with age; longest observed stem is 32 cm. Diameter of main stems — Varying with age; largest stem diameter observed stem is 7.5 cm. Internode length — From 6.0 to 9.0 cm. Attitude — Upright and outward. Cross-section — Rounded. Texture — Glabrous; succulent. Luster — Slightly to moderately glossy. Strength — Strong. Fragrance — None. Color, juvenile — Yellow-green, nearest to RHS 144B. Color, mature — Green, nearest to RHS 143A. Color at internodes — Green, nearest to RHS 143A. Color of the oldest wood — Yellow-green, nearest to in between RHS 147A and 148A but darker; axially striped greyed-brown, nearest to RHS 197B.

*Lateral branches*.—Quantity of lateral branches — 14. Length of lateral branches — Approximately 7.8 cm. Diameter of lateral branches — Approximately 0.9 cm. Internode length — Approximately 1.7 cm. Attitude — At an average angle of 35 degrees to vertical, varying between 20 and 50 degrees. Cross-section — Rounded. Texture — Glabrous; succulent. Luster — Slightly to moderately glossy. Strength — Strong. Fragrance — None. Color, juvenile — Yellow-green, nearest to RHS 144B. Color, mature — Green, nearest to RHS 143A. Color at internodes — Green, nearest to RHS 143A.

Foliage:

*Arrangement*.—Opposite.

*Division*.—Simple.

*Quantity*.—10 paired leaves per lateral branch.

*Attitude*.—Upward.

*Fragrance*.—None fragrant.

*Lamina*.—Shape — Narrow spatulate; tubular. Aspect — Varying from strongly convex to tubular. Dimensions — 5.9 cm long and 1.6 cm wide; convex leaves are 0.7 cm thick and tubular leaves are 1.0 cm thick. Thickness — Approximately 0.5 cm. Apex — Convex leaves are obtuse; tubular leaves are irregular cup-shaped. Base — Long cuneate. Margin — Entire. Texture of top surface — Glabrous, succulent, and glossy. Texture of bottom surface — Glabrous, succulent, and glossy. Color — Juvenile foliage, adaxial surface — Green, nearest to in between RHS 143A and 143B; slightly darker towards the apex, nearest to RHS 143A. Juvenile foliage, abaxial surface — Green, nearest to in between RHS 143A and 143B; slightly darker towards the apex, nearest to RHS 143A. Mature foliage, adaxial surface — Convex leaves are green, nearest to RHS NN137B; tubular leaves are green, nearest to RHS NN137A but slightly darker. Mature foliage, abaxial surface — Convex leaves are green, nearest to RHS NN137A; tubular leaves are green, nearest to RHS NN137A but slightly darker. Venation — No veins are visible.

*Petiole*.—No petioles present, leaves sessile.

Inflorescence: No flowering has been observed to date.

COMPARISON WITH THE PARENT PLANT

Plants of the new cultivar 'OVCRTR' differs from the parent, *Crassula* 'Hobbit' (not patented), in the following characteristics described in Table 1 below.

TABLE 1

| Characteristic | 'OVCRTR' | 'Hobbit' |
|---|---|---|
| Growth habit. | Less compact. | More compact. |
| Branching habit. | Fewer lateral branches. | More lateral branches. |

TABLE 1-continued

| Characteristic | 'OVCRTR' | 'Hobbit' |
|---|---|---|
| Leaf shape. | Less tubular. | More tubular. |
| Leaf apex. | Obtuse to cup-shaped. | Cup-shaped. |
| Leaf thickness. | Thicker than 'Hobbit'. | Thinner than 'OVCRTR'. |

COMPARISON WITH THE CLOSEST KNOWN COMPARATOR

Plants of the new cultivar 'OVCRTR' differs from the commercial variety, *Crassula* 'ET FINGERS' (not patented) in the following characteristics described in Table 2 below.

TABLE 2

| Characteristic | 'OVCRTR' | 'ET FINGERS' |
|---|---|---|
| Growth habit. | Less compact. | More compact. |
| General coloration of the foliage. | Darker green. | Lighter green. |
| Abundance of foliage. | More abundant. | Less abundant. |

That which is claimed is:

1. A new and distinct variety of *Crassula* plant named 'OVCRTR', substantially as described and illustrated herein.

* * * * *